(12) United States Patent
Ohkuma et al.

(10) Patent No.: US 8,759,524 B2
(45) Date of Patent: Jun. 24, 2014

(54) PRODUCTION PROCESS OF OPTICALLY ACTIVE 3-QUINUCLIDINOL DERIVATIVE

(71) Applicants: Takeshi Ohkuma, Sapporo (JP); Noriyoshi Arai, Sapporo (JP); Masaya Akashi, Oiso-cho (JP); Hirohito Oooka, Hadano (JP); Tsutomu Inoue, Chigasaki (JP)

(72) Inventors: Takeshi Ohkuma, Sapporo (JP); Noriyoshi Arai, Sapporo (JP); Masaya Akashi, Oiso-cho (JP); Hirohito Oooka, Hadano (JP); Tsutomu Inoue, Chigasaki (JP)

(73) Assignee: Nippon Soda Co., Ltd., Tokyo (JP)

(*) Notice: Subject to any disclaimer, the term of this patent is extended or adjusted under 35 U.S.C. 154(b) by 0 days.

(21) Appl. No.: 13/858,586

(22) Filed: Apr. 8, 2013

(65) Prior Publication Data

US 2013/0225824 A1 Aug. 29, 2013

Related U.S. Application Data

(63) Continuation of application No. 12/676,301, filed as application No. PCT/JP2008/065746 on Sep. 2, 2008, now Pat. No. 8,436,181.

(30) Foreign Application Priority Data

Sep. 6, 2007 (JP) ................. 2007-230973
Feb. 13, 2008 (JP) ................. 2008-032311

(51) Int. Cl.
*C07D 453/02* (2006.01)

(52) U.S. Cl.
USPC .......................... 546/137; 546/133

(58) Field of Classification Search
CPC ............................. C07D 453/02; A61K 31/44
See application file for complete search history.

(56) References Cited

U.S. PATENT DOCUMENTS

| | | | |
|---|---|---|---|
| 6,218,575 B1 | 4/2001 | Klingler et al. | |
| 6,410,749 B1 | 6/2002 | Katayama et al. | |
| 8,207,379 B2 * | 6/2012 | Akashi et al. | 564/358 |
| 2001/0037026 A1 | 11/2001 | Crameri et al. | |
| 2003/0045727 A1 | 3/2003 | Nakano et al. | |
| 2008/0027249 A1 | 1/2008 | Puentener et al. | |
| 2009/0216019 A1* | 8/2009 | Noyori et al. | 546/8 |

FOREIGN PATENT DOCUMENTS

| | | |
|---|---|---|
| EP | 1 650 207 | 4/2006 |
| EP | 1 867 654 | 12/2007 |
| JP | 10-130289 | 5/1998 |
| JP | 11-189600 | 7/1999 |
| JP | 2002-284790 | 10/2002 |
| JP | 2003/277380 A1 * | 2/2003 |
| JP | 2003-176266 | 6/2003 |
| JP | 2003-277380 | 10/2003 |
| JP | 2003/277380 A1 * | 10/2003 |
| JP | 2004-292434 | 10/2004 |
| JP | 2005-068113 | 3/2005 |
| JP | 2005-306804 | 11/2005 |
| JP | 2006-063028 | 3/2006 |
| JP | 2008-088089 | 4/2008 |
| JP | 2008-088090 | 4/2008 |
| WO | 02/04401 | 1/2002 |
| WO | WO 2004/007506 | 1/2004 |
| WO | 2006/103756 | 5/2006 |
| WO | WO 2006/103756 A1 * | 5/2006 |
| WO | 2006/103756 | 10/2006 |

OTHER PUBLICATIONS

Samec, JSM. et al. Mechanistic aspects of transition metal-catalyzed hydrogen transfer reactions. Chemical Society Reviews. 2006, vol. 35, p. 247.*
Noyori, R. et al. BINAP/1,4-Diamine-Ruthenium(II) Complexes for Efficient Asymmetric Hydrogenation of 1-Tetralones and Analogues. Organic Letters. 2004, vol. 6, p. 2682.*
Japanese Patent Office, International Search Report (translated) mailed Nov. 25, 2008, from related International Patent Application No. PCT/JP2008/065746.
European Search Report mailed Mar. 4, 2011, issued during the prosecution of EP 08829356.8, 5 pages.
Office Action from related case, Japanese Patent Application Serial No. 2009-531229, dated Aug. 7, 2012.
Samec, JSM. et al.; Mechanistic Aspects of transition Metal-Catalyzed Hydrogen transfer reactions; Chemical Society Reviews; 2006; vol. 35, p. 247.

(Continued)

*Primary Examiner* — Rita Desai
*Assistant Examiner* — Ben S Michelson
(74) *Attorney, Agent, or Firm* — Kenyon & Kenyon, LLP

(57) ABSTRACT

A process is provided for efficiently producing an optically active 3-quinuclidinol derivative of high optical purity using a readily available ruthenium compound as an asymmetric reduction catalyst. This process is a process for producing an optically active 3-quinuclidinol derivative represented by the following formula (III) comprising asymmetrically hydrogenating a 3-quinuclidinone derivative represented by the following formula (I) in the presence of a ruthenium compound (II) represented by formula (II): $Ru(X)(Y)(Px)_n[R^1R^2C^*(NR^3R^4)-A-R^5R^6C^*(NR^7R^8)]$ (in the formulas, R represents a hydrogen atom or C7 to C18 aralkyl group and the like, X and Y represent hydrogen atoms or halogen atoms and the like, Px represents a phosphine ligand, n represents 1 or 2, R1 to R8 represent hydrogen atoms or C1 to C20 alkyl groups and the like, * represents an optically active carbon atom and A represents an ethylene group and the like).

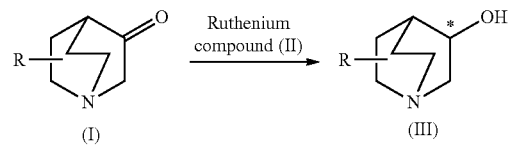

2 Claims, No Drawings

(56) References Cited

OTHER PUBLICATIONS

Non-Final Office Action mailed on Nov. 23, 2011, issued in the parent U.S. Appl. No. 12/676,301.
Tani, Kazuhide, et al., "Rh(I) Complexes Containing Fully Alkylated Mono- and Diphosphine Ligands as Highly Active Hydrogenation Catalysts for Carbonyl Compounds", Chemistry Letters, 1982, No. 3, pp. 261-264.
Burk, Mark J., et al., "Efficient Rhodium-Catalyzed Hydrogenation of Aldehydes and Ketones", Tetrahedron Letters, 1994, vol. 35, No. 28, pp. 4963-4966.
Zhang, Xiaoyong, et al., "Asymmetric Hydrogenation of Cycloalkanones Catalyzed by BINAP-Ir(I)-Aminophosphine Systems", Journal of the American Chemical Society, Apr. 21, 1993, vol. 115, No. 8, pp. 3318-3319.
Doucet, Henri, et al., "*trans*-[RuCl$_2$(phosphane)$_2$(1,2-diamine)] and Chiral *trans*-[RuCl$_2$(diphosphane)(1,2-diamine): Shelf-Stable Precatalysts for the Rapid, Productive, and Stereoselective Hydrogenation of Ketones", Angewandte Chemie International Edition, 1998, vol. 37, No. 12, pp. 1703-1707.
European Search Report dated Oct. 26, 2011, issued for EP 09730145.1, 5 pages.
International Search Report, International PCT Application No. PCT/JP2009/001569, mailed Jun. 23, 2009, 8 pages (Translated).
Office Action issued in the U.S. Appl. No. 12/936,496, dated Jan. 26, 2012, 6 pages.

\* cited by examiner

PRODUCTION PROCESS OF OPTICALLY ACTIVE 3-QUINUCLIDINOL DERIVATIVE

CROSS-REFERENCE TO RELATED APPLICATIONS

This application is a continuation application of U.S. application Ser. No. 12/676,301, filed on Mar. 3, 2010, which is a national phase application of PCT/JP2008/065746 filed on Sept. 2, 2008 which claims priortity under 35 U.S.C. 119 to Japanese Patent Application Nos. 2008-032311 filed on Feb. 13, 2008 and 2007-230973 filed on Sept. 6, 2007.

TECHNICAL FIELD

The present invention relates to a process for producing optically active 3-quinuclidinol derivatives that are useful as production raw materials of physiologically active substances, and particularly pharmaceuticals.

The present application claims priority on Japanese Patent Application No. 2007-230973, filed on Sep. 6, 2007, and Japanese Patent Application No. 2008-032311, filed on Feb. 13, 2008, the contents of which are incorporated herein by reference.

BACKGROUND OF THE ART

Many alkaloids, and particularly those compounds having an azabicyclo ring structure, are useful as physiologically active substances. In particular, optically active 3-quinuclidinol derivatives are important compounds as production raw materials of pharmaceuticals.

A conventionally known process for industrial production of optically active 3-quinuclidinol consists of direct asymmetric hydrogenation of 3-quinuclidinone using inexpensive hydrogen gas for the hydrogen source in the presence of an asymmetric hydrogenation catalyst (Patent Documents 1 to 4).

In this production process, an optically active transition metal complex having an optically active diphosphine and 1,2-diamine as ligands is used for the asymmetric hydrogenation catalyst.

For example, the optically active transition metal complex described in Patent Document 1 has a bisbinaphthyl compound derivative having an asymmetric axis for the optically active diphosphine ligand, that described in Patent Document 2 has a bisbiphenyl compound derivative having an asymmetric axis for the optically active diphosphine ligand, that described in Patent Document 3 has a ferrocene compound derivative having an optically active group in a side chain thereof for the optically active diphosphine ligand, and that described in Patent Document 4 has an alkane compound derivative having an asymmetric carbon for the optically active diphosphine ligand. In addition, the optically active transition metal complexes of all of these patent documents have optically active or racemic 1,2-diamine compounds as diamine ligands. Hydrogenation reactions are allowed to proceed under mild conditions by all of the asymmetric hydrogenation catalysts described in these publications.

However, the processes described in Patent Documents 1 and 3 have low enantiomeric excess for the resulting quinuclidinol and low catalyst efficiency, the process described in Patent Document 2 has low catalyst efficiency, and the process described in Patent Document 4 has low enantiomeric excess for the resulting quinuclidinol.

Thus, there is a desire for the development of a process that enables direct asymmetric hydrogenation of 3-quinuclidinone having high attainment rates for both enantiomeric excess and catalyst efficiency.

[Patent Document 1] Japanese Unexamined Patent Application, First Publication No. 2003-277380

[Patent Document 2] Japanese Unexamined Patent Application, First Publication No. 2005-306804

[Patent Document 3] Japanese Unexamined Patent Application, First Publication No. 2004-292434

[Patent Document 4] International Publication No. WO 2006-103756

DISCLOSURE OF THE INVENTION

Problems to be Solved by the Invention

With the foregoing in view, an object of the present invention is to provide a process for efficiently producing 3-quinuclidinol derivatives of high optical purity by direct asymmetric hydrogenation of 3-quinuclidinone derivatives at high attainment rates for both enantiomeric excess (or enantiomeric excess and diastereomeric excess) and catalyst efficiency.

Means for Solving the Problems

In order to solve the aforementioned problems, the inventors of the present invention conducted extensive studies on processes for direct asymmetric hydrogenation of 3-quinuclidinone derivatives using inexpensive hydrogen gas for the hydrogen source in the presence of an asymmetric hydrogenation catalyst. As a result, the inventors of the present invention found that the use of a readily available optically active ruthenium metal complex having a diphosphine ligand and a 1,4-dimaine ligand for the asymmetric hydrogenation catalyst enabled 3-quinuclidinol derivatives of high optical purity to be produced at high yield by direct asymmetric hydrogenation of 3-quinuclidinone derivatives at high attainment rates for both enantiomeric excess (or enantiomeric excess and diastereomeric excess) and catalyst efficiency, thereby leading to completion of the present invention.

Thus, according to the present invention, a process for producing optically an active 3-quinuclidinol derivative is provided as indicated in (1) to (5) below.

(1) A process is provided for producing an optically active 3-quinuclidinol derivative represented by formula (III):

(III)

(wherein, R represents a hydrogen atom, an unsubstituted or substituted C1 to C20 alkyl group, an unsubstituted or substituted C2 to C20 alkenyl group, an unsubstituted or substituted C3 to C8 cycloalkyl group, an unsubstituted or substituted C5 to C6 cycloalkenyl group, an unsubstituted or substituted C7 to C18 aralkyl group or an unsubstituted or substituted C6 to C18 aryl group, and * represents an optically active carbon atom), comprising: asymmetrically hydrogenating a 3-quinuclidinone derivative represented by formula (I):

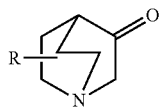
(I)

(wherein,
R is the same as previously defined) in the presence of a ruthenium compound represented by formula (II):

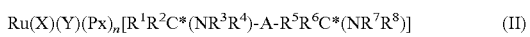
$$Ru(X)(Y)(Px)_n[R^1R^2C^*(NR^3R^4)\text{-}A\text{-}R^5R^6C^*(NR^7R^8)] \qquad (II)$$

(wherein,
X and Y respectively and independently represent a hydrogen atom, a halogen atom, a carboxylate, a hydroxyl group or a C1 to C20 alkoxy group;
Px represents a phosphine ligand;
n represents 1 or 2;
$R^1$ to $R^8$ respectively and independently represent a hydrogen atom, an unsubstituted or substituted C1 to C20 alkyl group, an unsubstituted or substituted C2 to C20 alkenyl group, an unsubstituted or substituted C3 to C8 cycloalkyl group, an unsubstituted or substituted C5 to C6 cycloalkenyl group, an unsubstituted or substituted C7 to C18 aralkyl group or an unsubstituted or substituted C6 to C18 aryl group, or either of $R^1$ and $R^2$ may bond with either of $R^3$ and $R^4$, and either of $R^5$ and $R^6$ may bond with either of $R^7$ and $R^8$, to form a ring;
* is the same as previously defined; and,
A represents an unsubstituted or substituted C1 to C3 alkylene group that may have ether bond(s), an unsubstituted or substituted C3 to C8 cycloalkylene group, an unsubstituted or substituted arylene group or an unsubstituted or substituted divalent heterocyclic group, and in the case A is an unsubstituted or substituted C1 to C3 alkylene group, either of $R^1$ and $R^2$ and either of $R^5$ and $R^6$ may bond to form a ring).
(2) A process for producing an optically active 3-quinuclidinol derivative represented by formula (III-1):

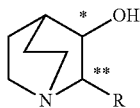
(III-1)

(wherein,
R and * are the same as previously defined, and ** represents an optically active carbon atom in the case R is other than a hydrogen atom), comprising: asymmetrically dehydrogenating a 3-quinuclidinone derivative represented by formula (I-1):

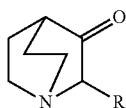
(I-1)

(wherein, R is the same as previously defined) in the presence of a ruthenium compound represented by the formula (II).

(3) The process for producing an optically active 3-quinuclidinol derivative described in (1) or (2) above, wherein the ruthenium compound represented by formula (II) is a ruthenium compound represented by formula (II-1):

$$Ru(X)(Y)(Px)_n[R^1C^*H(NR^3R^4)\text{-}A\text{-}R^1C^*H(NR^3R^4)] \qquad (II\text{-}1)$$

(wherein, X, Y, Px, n, $R^1$, $R^3$, $R^4$, * and A are the same as previously defined).
(4) The process for producing an optically active 3-quinuclidinol derivative described in (1) or (2) above, wherein the ruthenium compound represented by formula (II) is a ruthenium compound represented by formula (II-2):

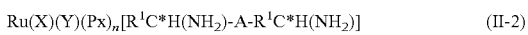
$$Ru(X)(Y)(Px)_n[R^1C^*H(NH_2)\text{-}A\text{-}R^1C^*H(NH_2)] \qquad (II\text{-}2)$$

(wherein, X, Y, Px, n, $R^1$, * and A are the same as previously defined).
(5) The process for producing an optically active 3-quinuclidinol derivative described in (1) or (2) above, wherein the ruthenium compound represented by formula (II) is a ruthenium compound represented by formula (II-3):

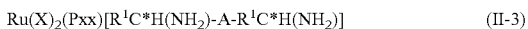
$$Ru(X)_2(Pxx)[R^1C^*H(NH_2)\text{-}A\text{-}R^1C^*H(NH_2)] \qquad (II\text{-}3)$$

(wherein, X, $R^1$, * and A are the same as previously defined, and Pxx represents an optically active phosphine ligand).

Effects of the Invention

According to the present invention, an optically active 3-quinuclidinol derivative of high optical purity can be produced at high attainment rates for enantiomeric excess or diastereomeric excess and catalyst efficiency by using a readily available ruthenium compound as an asymmetric reduction catalyst.

BEST MODE FOR CARRYING OUT THE INVENTION

The following provides a detailed explanation of the present invention.
The present invention is a process for producing an optically active 3-quinuclidinol derivative represented by the formula (III) that comprises asymmetric dehydrogenation of a 3-quinuclidinone derivative represented by the formula (I) in the presence of a ruthenium compound represented by the formula (II).

3-Quinuclidinone Derivative (I)
In the present invention, the 3-quinuclidinone derivative represented by the formula (I) (to be referred to as the "3-quinuclidinone derivative (I)") is used as a starting raw material.
In the formula (I), R represents a hydrogen atom, an unsubstituted or substituted C1 to C20 alkyl group, an unsubstituted or substituted C2 to C20 alkenyl group, an unsubstituted or substituted C3 to C8 cycloalkyl group, an unsubstituted or substituted C5 to C6 cycloalkenyl group, an unsubstituted or substituted C7 to C18 aralkyl group or an unsubstituted or substituted C6 to C18 aryl group.
Examples of C1 to C20 alkyl groups include a methyl group, ethyl group, n-propyl group, i-propyl group, n-butyl group, s-butyl group, t-butyl group, n-pentyl group and n-hexyl group.
Examples of C2 to C20 alkenyl groups include a vinyl group, 1-propenyl group, 2-propenyl group, 1-n-butenyl group, 1-s-butenyl group, 1,3-butadienyl group, 1-n-pentenyl group, 2-n-pentenyl group, 3-n-pentenyl group and 2-n-hexenyl group.
Examples of C3 to C8 cycloalkyl groups include a cyclopropyl group, cyclobutyl group, cyclopentyl group and cyclohexyl group.

Examples of C5 to C6 cycloalkenyl groups include a 1-cyclopentenyl group, 2-cyclopentenyl group, 1-cyclohexenyl group, 2-cyclohexenyl group and 3-cyclohexenyl group.

Examples of C7 to C18 aralkyl groups include a benzyl group, α,α-dimethylbenzyl group, phenethyl group and benzhydryl group.

Examples of C6 to C18 aryl groups include a phenyl group, 1-naphthyl group, 2-naphthyl group and 3-anthracenyl group.

There are no particular limitations on the type or number of substituents of the C1 to C20 alkyl groups and C2 to C20 alkenyl groups provided they are within a chemically acceptable range. Examples of these substituents include halogen atoms such as a fluorine atom, chlorine atom, bromine atom or iodine atom; hydroxyl groups; C1 to C20 alkoxy groups such as a methoxy group, ethoxy group, n-propoxy group, i-propoxy group, n-butoxy group, s-butoxy group, i-butoxy group or t-butoxy group; C7 to C18 aralkyloxy groups such as a benzyloxy group, α,α-dimethylbenzyloxy group or phenethyloxy group; acylamino groups such as an acetylamino group or benzoylamino group; sulfonylamino groups such as a methanesulfonylamino group or toluenesulfonylamino group; N-alkyl-N-acylamino groups such as an N-methyl-N-acetylamino group, N-ethyl-N-acetylamino group, N-methyl-N-benzoylamino group or N-ethyl-N-acylamino group; N-alkyl-N-alkylsulfonylamino groups such as N-methyl-N-methylsulfonylamino group or N-ethyl-N-methylsulfonylamino group; phthalimido groups; and oxygen-containing heterocyclic groups such as a furanyl group, pyranyl group or dioxolanyl group.

There are no particular limitations on the type or number of substituents of the C7 to C18 aralkyl groups, C6 to C18 aryl groups, C3 to C8 cycloalkyl groups and C5 to C6 cycloalkenyl groups provided they are within a chemically acceptable range.

Examples of these substituents include halogen atoms such as a fluorine atom, chlorine atom, bromine atom or iodine atom; hydroxyl groups; C1 to C20 alkoxy groups such as a methoxy group, ethoxy group, n-propoxy group, i-propoxy group, n-butoxy group, s-butoxy group, i-butoxy group or t-butoxy group; C7 to C18 aralkyloxy groups such as a benzyloxy group, α,α-dimethylbenzyloxy group or phenethyloxy group; acylamino groups such as an acetylamino group or benzoylamino group; sulfonylamino groups such as a methanesulfonylamino group or toluenesulfonylamino group; N-alkyl-N-acylamino groups such as an N-methyl-N-acetylamino group, N-ethyl-N-acetylamino group, N-methyl-N-benzoylamino group or N-ethyl-N-acylamino group; N-alkyl-N-alkylsulfonylamino groups such as N-methyl-N-methylsulfonylamino group or N-ethyl-N-methylsulfonylamino group; oxygen-containing heterocyclic groups such as a phthalimido group, furanyl group, pyranyl group or dioxolanyl group; C1 to C20 alkyl groups such as a methyl group, ethyl group, n-propyl group, i-propyl group, n-butyl group, s-butyl group, t-butyl group, n-pentyl group or n-hexyl group; C3 to C8 cycloalkyl groups such as a cyclopropyl group, cyclobutyl group or cyclopentyl group; C2 to C20 alkenyl groups such as a vinyl group, n-propenyl group, i-propenyl group, n-butenyl group, sec-butenyl group, 1,3-butadienyl group, n-pentenyl group, 2-pentenyl group, 3-pentenyl group or hexenyl group; C5 to C6 cycloalkenyl groups such as a 1-cyclopentenyl group, 2-cyclopentenyl group, 1-cyclohexenyl group, 2-cyclohexenyl group or 3-cyclohexenyl group; C7 to C18 aralkyl groups such as a benzyl group, α,α-dimethylbenzyl group or phenethyl group; and C6 to C18 aryl groups such as a phenyl group, 1-naphthyl group, 2-naphthyl group or 3-anthracenyl group.

There are no particular limitations on the 3-quinuclidinone derivative represented by formula (I) with respect to the steric configuration of carbon atoms substituted by R when R is not a hydrogen atom, and may an optically active form or racemic mixture.

The 3-quinuclidinone derivative represented by formula (I) is preferably a compound represented by formula (I-1):

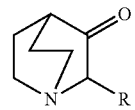
(I-1)

(wherein, R is the same as previously defined), and more preferably a compound represented by the following formulas.

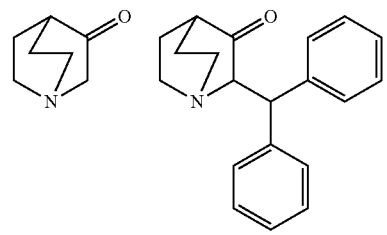

Ruthenium Compound (II)

In the present invention, the ruthenium compound represented by the formula (II) (to be referred to as the "ruthenium compound (II)") is used as an asymmetric hydrogenation catalyst.

In the formula (II), X and Y respectively and independently represent a hydrogen atom (hydride), halogen atom (halide ion), carboxylate, hydroxyl group (hydroxide ion) or C1 to C20 alkoxy group.

Examples of the halogen atom include a fluorine atom, chlorine atom, bromine atom and iodine atom.

Examples of the carboxylate include anions of C2 to C20 carboxylic acids such as acetic acid, propionic acid or n-butanoic acid.

Examples of the C1 to 20 alkoxy groups include a methoxy group, ethoxy group, n-propoxy group, i-propoxy group, n-butoxy group, s-butoxy group, i-butoxy group and t-butoxy group.

Px represents a phosphine ligand, there are no particular limitations thereon provided it can be a ligand of the ruthenium compound represented by the formula (II), and it is preferably an optically active ligand.

Examples of the phosphine ligand include monodentate phosphine ligands represented by the formula: $PR_AR_BR_C$, and bidentate phosphine ligands represented by the formula:

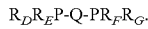

In the formulas $PR_AR_BR_C$ and $R_DR_EP\text{-}Q\text{-}PR_FR_G$, $R_A$ to $R_G$ respectively and independently represent an unsubstituted or substituted C1 to C20 alkyl group such as a methyl group, ethyl group, n-propyl group, i-propyl group, n-butyl group, s-butyl group, t-butyl group, n-pentyl group or n-hexyl group; an unsubstituted or substituted C6 to C14 aryl group such as a phenyl group, 1-naphthyl group or 2-naphthyl group; or an unsubstituted or substituted C3 to C8 cycloalkyl group such as a cyclopropyl group, cyclopentyl group or cyclohexyl group.

In addition, any two of $R_A$, $R_B$ and $R_C$ may bond to form an unsubstituted or substituted carbon ring, or $R_D$ and $R_E$ or $R_F$ and $R_G$ may bond to form an unsubstituted or substituted carbon ring.

Moreover, two of $R_A$, $R_B$ and $R_C$ may bond to form an unsubstituted or substituted heterocyclic group, and $R_D$ and $R_E$ and/or $R_F$ and $R_G$ may bond to form an unsubstituted or substituted C3 to C6 heterocyclic group such as a phosphotane group, phosphorane group, phosphinane group or phosphepane group.

Q represents an unsubstituted or substituted C1 to C5 alkylene group such as a methylene group, ethylene group, trimethylene group or propylene group; an unsubstituted or substituted C3 to C8 cycloalkylene group such as a xylenediyl group, cyclopropylene group, cyclobutylene group, cyclopentylene group, cyclohexylene group or bicycloheptenediyl group; an unsubstituted or substituted C6 to C22 arylene group such as a phenylene group, naphthylene group, ferrocenylene group, 9,10-dihydroanthracenediyl group or xanthenediyl group (xanthene-4,5-diyl group); an unsubstituted or substituted divalent group of an axially symmetrical compound such as a 1,1'-biphenyl-2,2'-diyl group, 3,3'-bipyridyl-4,4'-diyl group, 4,4'-bipyridyl-3,3'-diyl group, 1,1'-binaphthyl-2,2'-diyl group or 1,1'-binaphthyl-7,7'-diyl group; or a divalent group of ferrocene.

There are no particular limitations on the type or number of the substituents of each of the unsubstituted or substituted groups indicated above provided they are within a chemically acceptable range. Specific examples of these substituents include the same substituents as those listed as examples of substituents of the aforementioned R, such as C7 to C18 aralkyl groups.

Specific examples of monodentate phosphine ligands represented by the formula: $PR_AR_BR_C$ include tertiary phosphines in which $R_A$, $R_B$ and $R_C$ are all the same groups such as trimethylphosphine, triethylphosphine, tributylphosphine, triphenylphosphine, tricyclohexylphosphine or tri(p-tolyl) phosphine; tertiary phosphines in which two of $R_A$, $R_B$ and $R_C$ are the same groups such as diphenylmethylphosphine, dimethylphenylphosphine, diisopropylmethylphosphine, 1-[2-(diphenylphosphino)ferrocenyl]ethyl methyl ether or 2-(diphenylphosphino)-2'-methoxy-1,1'-binaphthyl; and tertiary phosphines in which all of $R_A$, $R_B$ and $R_C$ are different such as cyclohexyl(O-anisyl)-methylphosphine, ethylmethylbutylphosphine, ethylmethylphenylphosphine or isopropylethylmethylphosphine.

Examples of bidentate phosphine ligands represented by the formula: $R_DR_EP-Q-PR_FR_G$ include bisdiphenylphosphinomethane, 1,2-bis(diphenylphosphino)ethane, 1,3-bis(diphenylphosphino)propane, 1,4-bis(diphenylphosphino) butane, 1,2-bis(dimethylphosphino)ethane, 1,3-bis(dimethylphosphino)propane, 9,9-dimethyl-4,5-bis [bis(2-methylphenyl)phosphino]xanthene (XANTPHOS) and 2,2'-bis(diphenylphosphino)-1,1'-binaphthyl (BINAP).

In addition, BINAP derivatives, which have a substituent such as a halogen atom, alkyl group, halogenated alkyl group, aryl group or alkoxy group on the naphthyl ring and/or benzene ring of BINAP, are also preferable examples of bidentate phosphine ligands.

Specific examples of the aforementioned BINAP derivatives include bidentate phosphine ligands such as 2,2'-bis(di-p-tolylphosphino)-1,1'-binaphthyl or 2,2'-bis[bis(3,5-dimethylphenyl)phosphino]-1,1'-binaphthyl; 1-[2-(diphenylphosphino)ferrocenyl]ethyldi-t-butylphosphine; 1-[2-(diphenylphosphino)ferrocenyl]ethyldiphenylphosphine; 1-[2-(diphenylphosphino)ferrocenyl]ethyldicyclohexylphosphine; bidentate phosphine ligands having a substituent such as a halogen atom, alkyl group, halogenated alkyl group, aryl group or alkoxy group on a benzene ring of the aforementioned ferrocene derivatives; 1-butoxycarbonyl-4-dicyclohexylphosphino-2-(diphenylphosphinomethyl) pyrrolidine; 1-butoxycarbonyl-4-diphenylphosphino-2-(diphenylphosphinomethyl)pyrrolidine;

2,2'-bis(dicyclohexylphosphino)-6,6'-dimethyl-1,1'-biphenyl; 2,2'-bis(diphenylphosphino)-6,6'-dimethoxy-1,1'-biphenyl (MeO-BIPHEP); 2,2'-bis(diphenylphosphino)-5,5'-dichloro-6,6'-dimethoxy-1,1'-biphenyl (Cl-MeO-BIPHEP); 5,5'-bis(diphenylphosphino)-4,4'-bi-1,3-benzodioxole (SEGPHOS); bidentate phosphine ligands having a substituent such as a halogen atom, alkyl group, halogenated alkyl group, aryl group or alkoxy group on a 1,3-benzodioxole ring and/or benzene ring of SEGPHOS; 2,3-bis(diphenylphosphino)butane; 1-cyclohexyl-1,2-bis-(diphenylphosphino) ethane; 2,3-O-isopropylidene-2,3-dihydroxy-1,4-bis-(diphenylphosphino)butane;

1,2-bis(2,5-diethylphosphorano)benzene (Et-DUPHOS); 1,2-bis(2,5-di-t-isopropylphosphorano)benzene; 1,2-bis(2,5-dimethylphosphorano)benzene (Me-DUPHOS); 5,6-bis(diphenylphosphino)-2-norbornene; N,N'-bis(diphenylphosphino)-N,N'-bis(1-phenylethyl) ethylenediamine; 1,2-bis (diphenylphosphino)propane; 2,3-bis(diphenylphosphino) butane (CHIRAPHOS); 2,4-bis(diphenylphosphino)pentane (BDPP); 4,5-bis(diphenylphosphinomethyl)-2,2'-dimethyl-1,3-dioxolane (DIOP);

C3-TUNEPHOS; PHANEPHOS; Me-BPE; SYNPHOS; SDP; 1,2-bis(t-butylmethylphosphino)ethane; 1,2-bis[(2-methoxyphenyl) (phenyl)phosphino]ethane (DIPAMP); 2,2', 6,6'-tetramethoxy-4,4'-bis(diphenylphosphino)-3,3'-bipyridine; and, 1-Boc-4-diphenylphosphino-2-(diphenylphosphinomethyl)pyrrolidine.

In addition, in bidentate phosphine ligands represented by the formula: $R_DR_EP-Q-PR_FR_G$, Q may bond with $R_D$ and $R_F$ to form a bisheterocycle containing a phosphorous atom. Examples of these bisheterocycles include bisphosphotane, bisphosphorane, bisphosphinane and bisphosphepane.

Specific examples of bidentate phosphine ligands represented by the formula: $R_DR_EP-Q-PR_FR_G$, in which Q has bonded with $R_D$ and $R_F$ to form a bisheterocycle containing a phosphorous atom include 1,1'-di-t-butyl-[2,2']-diphosphoranyl (TANGPHOS), 2,2'-di-t-butyl-2,3,2',3'-tetrahydro-1H, 1'H-[1,1']-biisophosphindolyl (DUANPHOS), 4,4'-di-t-butyl-4,4',5,5'-tetrahydro-3,3'-bi-3H-dinaphtho[2,1-c:1',2'-e] phosphepine (BINAPINE), and 1,2-bis{4,5-dihydro-3H-dinaphtho[1,2-c:2',1'-e]phosphepino}benzene (BINAPHANE).

In the formula (II), n represents 1 or 2.

In the formula (II), $[R^1R^2C*(NR^3R^4)-A-R^5R^6C*(NR^7R^8)]$ represents an optically active diamine ligand.

In formula (II), * indicates that the carbon atom is an optically active carbon atom.

$R^1$ to $R^8$ respectively and independently represent a hydrogen atom, an unsubstituted or substituted C1 to C20 alkyl group, an unsubstituted or substituted C2 to C20 alkenyl group, an unsubstituted or substituted C3 to C8 cycloalkyl group, an unsubstituted or substituted C5 to C6 cycloalkenyl group, an unsubstituted or substituted C7 to C18 aralkyl group or an unsubstituted or substituted C6 to C18 aryl group.

Specific examples of unsubstituted or substituted C1 to C20 alkyl groups, unsubstituted or substituted C2 to C20 alkenyl groups, unsubstituted or substituted C3 to C8 cycloalkyl groups, unsubstituted or substituted C5 to C6 cycloalkenyl groups, unsubstituted or substituted C7 to C18 aralkyl groups and unsubstituted or substituted C6 to C18 aryl groups of $R^1$ to $R^8$ include the same as those listed as examples for the aforementioned R.

In addition, either of $R^1$ and $R^2$ may bond with either of $R^3$ and $R^4$, and either of $R^5$ and $R^6$ may bond with either of $R^7$ and $R^8$, to form a ring. Examples of cyclic residues formed by either of $R^1$ and $R^2$ bonding with either of $R^3$ and $R^4$ or either of $R^5$ and $R^6$ bonding with either of $R^7$ and $R^8$ include a 2-pyrrolidinyl group, 2-indolyl group, 2-piperidinyl group, 1,2,3,4-tetrahydroisoquinolin-2-yl group and 1,2,3,4-tetrahydroxyisoquinolin-3-yl group.

Among these examples, $R^1$ to $R^8$ are all preferably hydrogen atoms from the viewpoint of ease of synthesis and availability.

In addition, in the case A described below is an unsubstituted or substituted C1 to C3 alkylene group, either of $R^1$ and $R^2$ may bond with either of $R^5$ and $R^6$ to form a ring.

* indicates that the carbon atom is an optically active carbon atom.

A represents an unsubstituted or substituted C1 to C3 alkylene group that may have an ether bond, an unsubstituted or substituted C3 to C8 cycloalkylene group, an unsubstituted or substituted C6 to C22 arylene group or an unsubstituted or substituted divalent heterocyclic group.

Examples of C1 to C3 alkylene groups that may have an ether bond of A include a methylene group, ethylene group, propylene group, trimethylene group or —CH$_2$—O—CH$_2$— group.

Examples of C3 to C8 cycloalkylene groups and C6 to C22 arylene groups of A include the same groups as those listed as examples for the aforementioned Q.

Examples of divalent heterocyclic groups of A include divalent heterocyclic groups of 5-membered rings such as furan-3,4-diyl, tetrahydrofuran-3,4-diyl, 1,3-dioxolan-4,5-diyl, 2-oxo-1,3-dioxolan-4,5-diyl, thiophen-3,4-diyl, pyrrol-3,4-diyl or 2-imidazolidinone-4,5-diyl; divalent heterocyclic groups of 6-membered rings such as 1,4-dioxolan-2,3-diyl, pyrazin-2,3-diyl or pyridazin-4,5-diyl; and, divalent condensed heterocyclic groups such as 1,4-benzoxolane-2,3-diyl.

There are no particular limitations on substituents in the aforementioned C1 to C3 alkylene groups that may have an ether bond, C3 to C8 cycloalkylene groups, C6 to C22 arylene groups and divalent heterocyclic groups provided they are chemically acceptable. Specific examples of these substituents include the same substituents as those listed as examples of substituents of C7 to C18 aralkyl groups of the aforementioned R.

Furthermore, in the case A is an ethylene group having respective substituents on different carbon atoms, two substituents of the ethylene group may bond to form a hydrocarbon ring. Specific examples of A in such cases include divalent hydrocarbon rings such as cyclopentan-1,2-diyl, cyclohexan-1,2-diyl and 1,2-phenylene.

The ruthenium compound (II) used in the present invention is preferably a ruthenium compound represented by the formula (II-1):

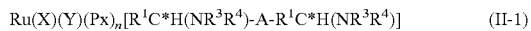

$$Ru(X)(Y)(Px)_n[R^1C^*H(NR^3R^4)-A-R^1C^*H(NR^3R^4)] \qquad (II\text{-}1)$$

(wherein, X, Y, Px, n, $R^1$, $R^3$, $R^4$, * and A are the same as previously defined), more preferably a ruthenium compound represented by the formula (II-2):

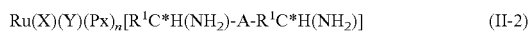

$$Ru(X)(Y)(Px)_n[R^1C^*H(NH_2)-A-R^1C^*H(NH_2)] \qquad (II\text{-}2)$$

(wherein, X, Y, Px, n, $R^1$, * and A are the same as previously defined), and particularly preferably a ruthenium compound represented by the formula (II-3):

$$Ru(X)_2(Pxx)[R^1C^*H(NH_2)-A-R^1CR(NH_2)] \qquad (II\text{-}3)$$

(wherein, X, $R^1$, * and A are the same as previously defined, and Pxx represents an optically active phosphine ligand).

More preferable examples of diamine ligands represented by the formula (II-3) include optically active diaminopentane, optically active diaminohexane, optically active bis(2-aminopropyl)ether, optically active bis(2-amino-2-phenylethyl)ether, optically active 1,3-diamino-1,3-diphenylpropane, optically active 1,4-diamino-1,4-diphenylbutane, optically active 1,4-diamino-1,4-dicyclohexylbutane, optically active 1,2-bis(1-aminoethyl) cyclopentane, optically active 1,1-bis(1-aminoethyl) cyclopentane, optically active 1,2-bis(1-aminoethyl) cyclohexane, optically active 1,2-bis(1-aminoethyl)benzene, 4R,5R-di (1R-aminoethyl) 2,2-dimethyl-[1,3]dioxolane, 4S, 5S-di(1S-aminoethyl) 2,2-dimethyl-[1,3]dioxolane, 4R, 5R-di(1S-aminoethyl) 2,2-dimethyl-[1,3]dioxolane and 4S, 5S-di(1R-aminoethyl) 2,2-dimethyl-[1,3]dioxolane.

Production of 3-Quinuclidinol Derivative

The production process of the present invention preferentially produces any optically active 3-quinuclidinol derivative (III) by an asymmetric hydrogenation reaction using the 3-quinuclidinone derivative (I) as a starting raw material and the ruthenium compound (II) as a hydrogenation catalyst.

The asymmetric hydrogenation reaction is carried out by asymmetrically reducing the 3-quinuclidinone derivative (I) in the presence of the ruthenium compound (II) and in the presence of hydrogen gas at a prescribed pressure or a hydrogen donor by adding a base as desired.

In addition, in the present invention, after forming the ruthenium compound (II) by adding a ruthenium complex having a phosphine ligand and a diamine compound which serve as production raw materials of the ruthenium compound (II) to reaction system separately, and adding a base as necessary, an asymmetric hydrogenation reaction can be carried out within the reaction system by adding a substrate to the reaction system, without removing the ruthenium compound (II).

Although varying according to the size of the reaction container and catalyst activity, the amount of the ruthenium compound (II) used as a catalyst is normally within the range of 1/5,000 to 1/200,000 times moles, and preferably within the range of 1/10,000 to 1/100,000 times moles, the reaction substrate in the form of the 3-quinuclidinone (I).

Examples of bases used include organic bases such as triethylamine, diisopropylethylamine, pyridine, 1,4-diazabicyclo[2.2.2]octane (DABCO) or 1,6-diazabicyclo[5.4.0]undec-7-ene (DBU); metal alkoxides such as sodium methoxide, sodium ethoxide, potassium t-butoxide, magnesium methoxide or magnesium ethoxide; organic lithium compounds such as n-butyl lithium; lithium amides such as lithium diisopropylamide (LDA) or lithium bistrimethylsilylamide; alkaline metal hydroxides such as lithium hydroxide, sodium hydroxide or potassium hydroxide; alkaline earth metal hydroxides such as magnesium hydroxide or calcium hydroxide; alkaline metal carbonates such as sodium carbonate or potassium carbonate; alkaline metal bicarbonates such as sodium bicarbonate or potassium bicarbonate; alkaline earth metal carbonates such as magnesium carbonate or calcium carbonate; and, metal hydrides such as sodium hydride or calcium hydride.

The amount of base added is 2 times moles or more and preferably within the range of 2 to 50,000 times moles the ruthenium compound (II).

The asymmetric hydrogenation reaction can be carried out in a suitable solvent. There are no particular limitations on the solvent used provided it solubilizes the substrate and catalyst without impairing the reaction. Specific examples of solvents include alcohols such as methanol, ethanol, n-propanol, i-propanol, i-butanol or benzyl alcohol; aromatic hydrocarbons such as benzene, toluene or xylene; aliphatic hydrocarbons such as pentane or hexane; halogenated hydrocarbons such as dichloromethane, chloroform, trichloromethane, carbon tetrachloride or 1,2-dichloroethane; ethers such as diethyl ether, tetrahydrofuran (THF), 1,2-dimethoxyethane or 1,4-dioxane; amides such as N,N-dimethylformamide (DMF), N,N-dimethylacetamide, 1,3-dimethylimidazolidine, 1,3-dimethyl-2-imidazolidinone, N-methylpyrrolidone or hexamethylphosphoric triamide (HMPT); nitriles such as acetonitrile or benzonitrile; and, DMSO.

One type of these solvents can be used alone or two or more types can be used as a mixture. Among these, alcohols are used preferably since the reaction products are alcohol compounds.

The amount of solvent used depends on the solubility of the 3-quinuclidinone derivative (I) and economic efficiency, and although the reaction also proceeds in the absence of solvent or in a state near highly diluted conditions depending on the case, the amount of solvent used is normally within the range of 10 to 10,000 parts by weight, and preferably within the range of 50 to 1,000 parts by weight, based on 100 parts by weight of the 3-quinuclidinone derivative (I).

The pressure of the hydrogen is normally $1\times10^5$ to $2\times10^7$ Pa, and is preferably within the range of $3\times10^5$ to $1\times10^7$ Pa from the viewpoint of practicality.

A hydrogen storage alloy or diimide and the like can be used for the hydrogen donor used. The amount used is normally within the range of 1 to 100 times equivalents the 3-quinuclidinone derivative (I).

The reaction temperature is normally within the range of −50 to +200° C. and preferably within the range of 0 to 100° C.

In addition, although varying according to the reaction substrate concentration and reaction conditions such as temperature and pressure, the reaction temperature is normally from several minutes to several days.

There are no particular limitations on the type of reaction, and the reaction may be of a batch type or continuous type.

Following completion of the reaction, isolation and purification are carried out using ordinary organic synthetic chemistry techniques to enable the obtaining of the optically active 3-quinuclidinol derivative (III).

Structures of target compounds can be identified and confirmed by known analytical means such as elementary analysis, NMR, IR or mass spectroscopy.

An optically active 3-quinuclidinol derivative obtained in the manner described above is useful as a production raw material of active ingredients of pharmaceuticals or production intermediates of those active ingredients.

3-Quinuclidinol Derivative (III)

According to the present invention, an optically active 3-quinuclidinol derivative represented by the formula (III) (to be referred to as the 3-quinuclidinol derivative (III)) can be obtained.

Namely, in the case of a compound represented by the formula (I), any 3-quinuclidinol derivative (III) having an optically active carbon atom indicated with an * can be obtained by asymmetric hydrogenation reaction using the ruthenium compound (II) as a hydrogenation catalyst. This is the result of any enantiomeric isomer being preferentially obtained corresponding to an enantiomer of the ruthenium compound (II) used.

In addition, in the present invention, the 3-quinuclidinol derivative represented by the formula (III-1) can be obtained in the case of using the 3-quinuclidinone derivative represented by the formula (I-1) as a starting raw material.

In the case of a compound represented by the formula (I-1), if a reaction is carried out by using as a starting raw material 3-quinuclidinone in which R in the formula is a hydrogen atom and using the ruthenium compound (II) as a catalyst, either of the 3-quinuclidinols (IIIa) and (IIIb) represented by the following formulas can be obtained.

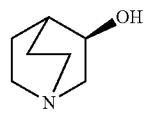

(IIIa)

(IIIb)

In addition, in the case of a compound represented by the formula (I-1), if an asymmetric hydrogenation reaction is carried out using a 3-quinuclidinone derivative represented by formula (I-1) as a starting raw material in which R in the formula is that other than a hydrogen atom and using the ruthenium compound (II) as a hydrogenation catalyst, either of the 3-quinuclidinol derivatives (IIIc) and (IIId) represented by the following formulas can be obtained:

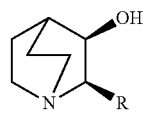

(IIIc)

(IIId)

(wherein, R is the same as previously defined).

An optically active 3-quinuclidinol derivative obtained by the production process of the present invention is useful as a production raw material of active ingredients of pharmaceuticals or production intermediates of those active ingredients.

EXAMPLES

Although the following provides a more detailed explanation of the present invention through examples thereof, the present invention is not limited to only these examples.

Furthermore, the apparatuses used to measure physical properties in each of the examples are as indicated below.

(1) Varian GEMINI-300 (300 MHz, Varian Inc.), JNM-A300 (300 MHz) and JNM-A400 (400 MHz, JEOL Ltd.)

(2) Measurement of optical rotation: Polarimeter, JASCO DIP-360 (Jasco Corp.)

(3) High-performance liquid chromatograph: LC-10Advp, SPD-10Avp (Shimadzu Corp.)

(4) Gas chromatograph: GC-17A, CR-7A Plus (Shimadzu Corp.) and GC-353B (GL Sciences Inc.)

The ruthenium compound (II) used was synthesized in accordance with the process described in Japanese Unexamined Patent Application, First Publication No. 2002-284790.

Example 1

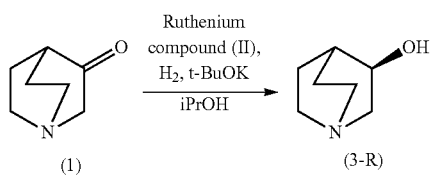

1.63 g (13 mmol) of the 3-quinuclidinone (I) were added to a 50 ml Schlenk tube and after reducing pressure inside the vessel with a vacuum pump, argon was sealed inside. This procedure was repeated three times to replace the inside of the vessel with argon. 12.7 ml of 2-propanol and 0.26 ml (0.26 mmol) of a 2-propanol solution of potassium tert-butoxide (1.0 M) were respectively added to the vessel with a glass syringe. After completely dissolving the 3-quinuclidinone using an ultrasonic device, the solution was frozen at the temperature of liquid nitrogen. After reducing the pressure inside the vessel with a vacuum pump, the solution was thawed using a heat gun. This freezing-degassing procedure was repeated three times to obtain a substrate solution.

A polytetrafluoroethylene-coated stirrer bar and 1.4 mg of the ruthenium compound (II) in the form of (S)-1,1'-binapthyl-2,2'-bis(di-p-tolyl) phosphine ruthenium (II) dichloride (2R,3R,4R,5R)-3,4-O-isopropylidenehexane-2,5-diamine complex (1.3 μmol, S/C=(substrate: 13 mmol)/(ruthenium compound (II): 1.3 μmol)=10,000) were added to a 100 ml stainless steel autoclave (provided with a glass inner tube) followed by replacing the inside of the vessel with argon. Next, the substrate solution was transferred to the autoclave using a polytetrafluoroethylene tube.

The autoclave was connected to a hydrogen tank using a hydrogen feed tube and hydrogen at 0.2 MPa was released 10 times to replace air inside the feed tube with hydrogen. Subsequently, hydrogen at 1.0 MPa was sealed in the autoclave vessel followed immediately by releasing hydrogen until the pressure reached 0.2 MPa, and this procedure was repeated 10 times to replace the inside of the vessel with hydrogen. Finally, hydrogen was filled to a pressure of 2.0 MPa followed by stirring for 5 hours at 20 to 25° C.

Following completion of the reaction, 146.1 ml (1.105 mmol) of distillation purified tetralin were added to the reaction solution as an internal standard followed by stirring to achieve uniformity. When the reaction mixture was analyzed by gas chromatography, 13 mmol of (R)-3-quinuclidinol (3-R) were determined to have been formed at a enantiomeric excess of 97% ee (R) (yield: 100%).

Example 2

The same reaction as Example 1 was carried out with the exception of using (S)-1,1'-binaphthyl-2,2'-bis(diphenyl) phosphine ruthenium (II) dichloride (2R,3R,4R,5R)-3,4-O-isopropylidenehexane-2,5-diamine complex for the ruthenium compound (II) to obtain (R)-3-quinuclidinol (3-R). S/C, conversion rate and enantiomeric excess are indicated below.

S/C: 10,000
Conversion rate: 100%
Enantiomeric excess: 97% ee(R)

Example 3

The same reaction as Example 1 was carried out with the exception of using (S)-1,1'-binaphthyl-2,2'-bis(diphenyl) phosphine ruthenium (II) dichloride (R,R)-hexane-2,5-diamine complex for the ruthenium compound (II) to obtain (R)-3-quinuclidinol (3-R). S/C, conversion rate and enantiomeric excess are indicated below.

S/C: 20,000
Conversion rate: 100%
Enantiomeric excess: 95% ee(R)

Example 4

1.63 g (13 mmol) of the 3-quinuclidinone (I), 1.1 mg (1.3 μmol) of {[(S)-(6,6'-dimethyl-1,1'-biphenyl-2,2'-diyl)-bis(diphenylphosphine)]ruthenium (II) dichloride (DMF)n} complex, 12.7 ml of 2-propanol and 31 μl (1.55 μmol) of a 0.05 M 2-propanol solution of (2R,3R,4R,5R)-3,4-O-isopropylidenehexane-2,5-diamine were added to an autoclave in which the inside had been replaced with argon followed by carrying out a degassing procedure and stirring for 30 minutes at room temperature. 0.26 mL (0.26 mmol) of a 2-propanol solution of potassium tert-butoxide (1.0 M) were added thereto followed by stirring for 16 hours at 20 to 25° C. at a hydrogen pressure of 2.0 MPa to obtain (R)-3-quinuclidinol (3-R). S/C, conversion rate and enantiomeric excess are indicated below.

S/C: 10,000
Conversion rate: 100%
Enantiomeric excess: 95% ee(R)

Example 5

1.63 g (13 mmol) of the 3-quinuclidinone (I), 1.1 mg (1.3 μmol) of {[(S)-(6,6'-dimethyl-1,1'-biphenyl-2,2'-diyl)-bis(di-p-tolylphosphine)]ruthenium (II) dichloride (DMF)n} complex, 12.7 ml of 2-propanol and 31 μl (1.55 μmol) of a 0.05 M 2-propanol solution of (2R,3R,4R,5R)-3,4-O-isopropylidenehexane-2,5-diamine were added to an autoclave in which the inside had been replaced with argon followed by carrying out a degassing procedure and stirring for 30 minutes at room temperature. 0.26 mL (0.26 mmol) of a 2-propanol solution of potassium tert-butoxide (1.0 M) were added thereto followed by stirring for 16 hours at 20 to 25° C. at a hydrogen pressure of 2.0 MPa to obtain (R)-3-quinuclidinol (3-R). S/C, conversion rate and enantiomeric excess are indicated below.

S/C: 10,000
Conversion rate: 100%
Enantiomeric excess: 96% ee(R)

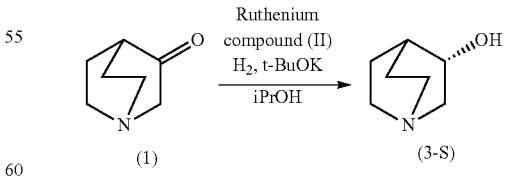

Example 6

The same reaction as Example 1 was carried out with the exception of using (R)-1,1'-binaphthyl-2,2'-bis(diphenyl) phosphine ruthenium (II) dichloride (1S,2S,3S,4S)-2,3-O- isopropylidene-1,4-diphenylbutane-1,4-diamine complex for the ruthenium compound (II) to obtain (S)-3-quinuclidinol (3-S). S/C, conversion rate and enantiomeric excess are indicated below.
S/C: 5,000
Conversion rate: 100%
Enantiomeric excess: 95% ee(S)

Example 7

The same reaction as Example 1 was carried out with the exception of using (R)-1,1'-binaphthyl-2,2'-bis(di-p-tolyl)phosphine ruthenium (II) dichloride (S,S)-hexane-2,5-diamine complex for the ruthenium compound (II) to obtain (S)-3-quinuclidinol (3-S). S/C, conversion rate and enantiomeric excess are indicated below.
S/C: 10,000
Conversion rate: 100%
Enantiomeric excess: 97% ee(S)

Example 8

The same reaction as Example 1 was carried out with the exception of using (R)-1,1'-binaphthyl-2,2'-bis(di-p-tolyl)phosphine ruthenium (II) dichloride (S,S)-1,4-diphenylbutane-1,4-diamine complex for the ruthenium compound (II) to obtain (S)-3-quinuclidinol (3-S). S/C, conversion rate and enantiomeric excess are indicated below.
S/C: 10,000
Conversion rate: 100%
Enantiomeric excess: 98% ee(S)

Example 9

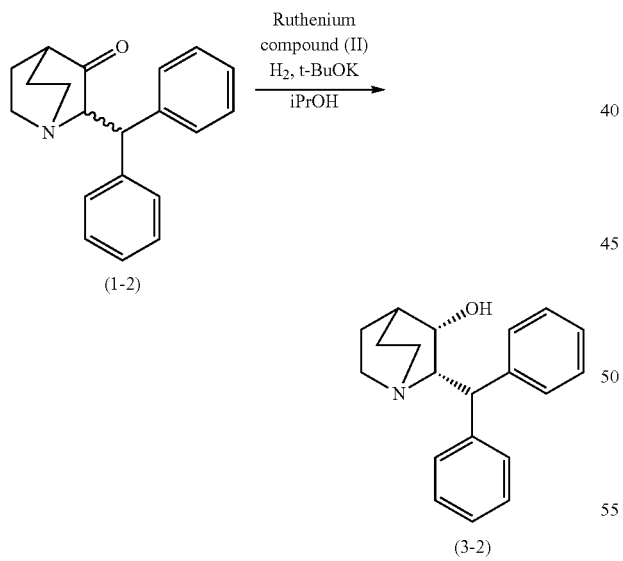

397.7 mg (1.30 mmol) of a racemic mixture of 2-benzhydrylquinuclidin-3-one (1-2) and 1.2 mg (1.3 µmol) of (S)-1,1'-binaphthyl-2,2'-bis(diphenyl)phosphine ruthenium (II) dichloride (R,R)-hexane-2,5-diamine complex were placed in an autoclave in which the inside had been replaced with argon. After adding 6.4 ml of 2-propanol thereto and degassing, 0.13 mL (0.13 mmol) of a 2-propanol solution of potassium tert-butoxide (1.0 M) were added thereto followed by stirring for 18 hours at 20 to 25° C. at a hydrogen pressure of 1.0 MPa. After concentrating the reaction solution, analysis of the crude purification product by 1H-NMR indicated that only the syn form had been formed. The reaction solution was then purified by silica gel column chromatography (developing solvent: n-hexane:ethyl acetate=3:1 (volume ratio)) to obtain 382 mg (1.30 mmol, yield: 96%) of (2S,3S)-2-benzhydrylquinuclidin-3-ol (3-2). The optical purity of this substance as measured by high-performance liquid chromatography (eluent: acetonitrile:0.02 M aqueous disodium hydrogen phosphate=6:4 (volume ratio), column: CHIRALCEL OD-RH, Daicel Chemical Industries, Ltd.) was 96% ee.

Example 10

The same reaction as Example 9 was carried out with the exception of using (S)-1,1'-binaphthyl-2,2'-bis(diphenyl)phosphine ruthenium (II) dichloride (2R,3R,4R,5R)-3,4-O-isopropylidenehexane-2,5-diamine complex for the ruthenium compound (II) to obtain (2S,3S)-2-benzhydrylquinuclidin-3-ol (3-2) at a yield of 99% and optical purity of >99% ee.

Example 11

The same reaction as Example 9 was carried out with the exception of using the compound represented by the following formula (12) for the ruthenium compound (II) to obtain (2S,3S)-2-benzhydrylquinuclidin-3-ol (3-2) at a yield of 96% and optical purity of >99.6% ee.

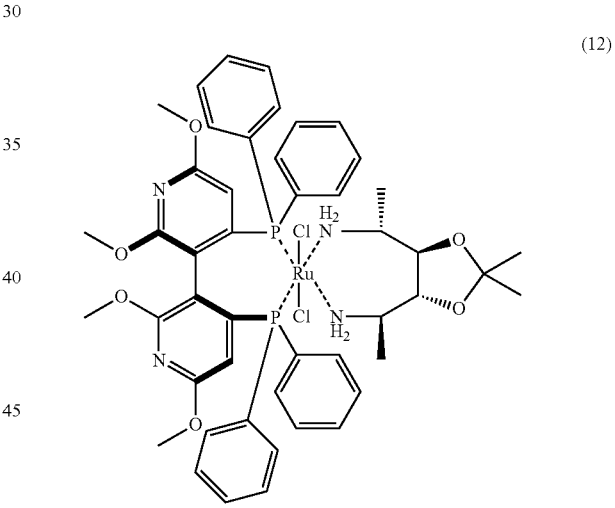

(12)

Example 12

398.0 mg (1.30 mmol) of a racemic mixture of 2-benzhydrylquinuclidin-3-one (1-2), 1.1 mg (1.3 µmol) of {[(S)-(6,6'-dimethyl-1,1'-biphenyl-2,2'-diyl)-bis(diphenylphosphine)]ruthenium (II) dichloride (DMF)n} complex, 6.4 ml of 2-propanol and 31 µl (1.55 µmol) of a 0.05 M 2-propanol solution of (2R,3R,4R,5R)-3,4-O-isopropylidenehexane-2,5-diamine were added to an autoclave in which the inside had been replaced with argon followed by degassing and stirring for 30 minutes at room temperature. 0.13 mL (0.13 mmol) of a 2-propanol solution of potassium tert-butoxide (1.0 M) were added thereto followed by stirring for 18 hours at 20 to 25° C. at a hydrogen pressure of 1 MPa. The same post-treatment procedure as Example 7 was carried out to obtain (2S,3S)-2-benzhydrylquinuclidin-3-ol (3-2) at a yield of 97% and optical purity of >99% ee.

INDUSTRIAL APPLICABILITY

According to the present invention, an optically active 3-quinuclidinol derivative of high optical purity can be produced at high attainment rates for enantiomeric excess or diastereomeric excess and catalyst efficiency by using a readily available ruthenium compound as an asymmetric reduction catalyst, thereby making the present invention extremely industrially useful.

The invention claimed is:

1. A process for producing an optically active 3-quinuclidinol derivative represented by formula (III-1):

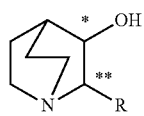
(III-1)

wherein, R represents a hydrogen atom or an unsubstituted or substituted C7 to C18 aralkyl group, and * represents an optically active carbon atom, and ** represents an optically active carbon atom in the case R is other than a hydrogen atom, comprising: asymmetrically hydrogenating a 3-quinuclidinone derivative represented by formula (I-1):

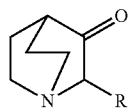
(I-1)

wherein, R is the same as previously defined in the presence of a ruthenium compound represented by the formula (II-2):

$$Ru(X)(Y)(Px)_n[R^1H(NH_2)C^*-A-C^*R^1H(NH_2)] \quad (II-2)$$

wherein,

X and Y represent a hydrogen atom or a chlorine atom;

Px represents a phosphine ligand selected from the group consisting of 2,2'-bis(diphenylphosphino)-1,1'-binaphthyl, 2,2'-bis(di-p-tolylphosphino)-1,1'-binaphthyl and 2,2'-bis[bis(3,5-dimethylphenyl)phosphine]-1,1'-binaphthyl;

n represents 1;

$R^1$ represents an unsubstituted or substituted C1 alkyl group or an unsubstituted or substituted C6 aryl group;

* is the same as previously defined; and,

A represents an unsubstituted or substituted C1 to C3 alkanediyl group or an unsubstituted or substituted divalent heterocyclic group.

2. The process for producing an optically active 3-quinuclidinol derivative according to claim 1, wherein the ruthenium compound represented by formula (II) is a ruthenium compound represented by formula (II-3):

$$Ru(X)_2(Pxx)[R^1H(NH_2)C^*-A-C^*R^1H(NH_2)] \quad (II-3)$$

wherein, X, $R^1$, * and A are the same as previously defined, and Pxx represents a phosphine ligand selected from the group consisting of 2,2'-bis(diphenylphosphino)-1,1'-binaphthyl, 2,2'-bis(di-p-tolylphosphino)-1,1'-binaphthyl and 2,2'-bis[bis(3,5-dimethylphenyl)phosphine]-1,1'-binaphthyl.

* * * * *